(12) United States Patent
Gutierrez

(10) Patent No.: US 11,376,432 B2
(45) Date of Patent: *Jul. 5, 2022

(54) NON-INVASIVE PERIOCULAR DEVICE FOR DRY-EYE TREATMENT

(71) Applicant: Twenty Twenty Therapeutics LLC, South San Francisco, CA (US)

(72) Inventor: Christian Gutierrez, Pacifica, CA (US)

(73) Assignee: TWENTY TWENTY THERAPEUTICS LLC, South San Francisco, CA (US)

( * ) Notice: Subject to any disclaimer, the term of this patent is extended or adjusted under 35 U.S.C. 154(b) by 92 days.

This patent is subject to a terminal disclaimer.

(21) Appl. No.: 16/829,563

(22) Filed: Mar. 25, 2020

(65) Prior Publication Data

US 2020/0306537 A1    Oct. 1, 2020

Related U.S. Application Data

(66) Substitute for application No. 62/824,111, filed on Mar. 26, 2019.

(51) Int. Cl.
*A61N 1/36* (2006.01)
*A61N 1/04* (2006.01)

(52) U.S. Cl.
CPC ....... *A61N 1/36046* (2013.01); *A61N 1/0472* (2013.01); *A61N 1/36031* (2017.08); *A61N 1/36034* (2017.08)

(58) Field of Classification Search
CPC ........... A61N 1/36046; A61N 1/36034; A61N 1/36031; A61N 1/0472; A61N 1/0476; A61F 9/00
See application file for complete search history.

(56) References Cited

U.S. PATENT DOCUMENTS 7,246,903 B2 * 7/2007 Bowers .................. G02C 7/046
351/159.24
8,585,204 B2   11/2013 Gravely et al.
(Continued)

FOREIGN PATENT DOCUMENTS

WO   WO-2012/139063 A2   10/2012
WO   WO-2016/065211 A1    4/2016
WO   WO-2017/100608 A1    6/2017

OTHER PUBLICATIONS

International Search Report and Written Opinion from the International Searching Authority for corresponding International Application No. PCT/US2020/024906, dated Jul. 31, 2020; 19 pages.

(Continued)

*Primary Examiner* — Catherine M Voorhees
(74) *Attorney, Agent, or Firm* — Haynes and Boone, LLP

(57) ABSTRACT

A periocular ring configured to be worn on an eye of a user that includes a plurality of electrodes spaced along the periocular ring; a microcontroller; and a lead assembly extending along at least a portion of the periocular ring; wherein the lead assembly extends between the microcontroller and the plurality of electrodes to operably couple the plurality of electrodes to the microcontroller; and wherein the microcontroller is configured to activate the plurality of electrodes via the lead assembly to stimulate a lacrimal gland of the user. The periocular ring has an opening that defines an innermost diameter; and wherein, when the periocular ring is worn on the eye of the user, a portion of the eye extends through the opening of the periocular ring.

17 Claims, 7 Drawing Sheets

(56) References Cited

U.S. PATENT DOCUMENTS

| | | | |
|---|---|---|---|
| 8,918,181 B2 | 12/2014 | Ackermann et al. | |
| 9,687,652 B2 | 6/2017 | Franke et al. | |
| 9,764,150 B2* | 9/2017 | Loudin | B29D 11/00038 |
| 2011/0184358 A1 | 7/2011 | Weiner et al. | |
| 2012/0130398 A1 | 5/2012 | Ackermann et al. | |
| 2013/0006326 A1* | 1/2013 | Ackermann | A61N 1/36046 |
| | | | 607/53 |
| 2014/0371565 A1* | 12/2014 | Glasser | A61B 5/6821 |
| | | | 600/383 |
| 2016/0121118 A1* | 5/2016 | Franke | A61N 1/36046 |
| | | | 607/53 |
| 2018/0035882 A1* | 2/2018 | Gutierrez | G02C 7/04 |
| 2018/0064941 A1* | 3/2018 | Ackermann | A61N 1/36046 |
| 2018/0092926 A1* | 4/2018 | Reich | A61F 9/0017 |
| 2018/0161579 A1* | 6/2018 | Franke | A61B 5/389 |
| 2018/0304079 A1 | 10/2018 | Kim et al. | |
| 2020/0306538 A1* | 10/2020 | Gutierrez | A61B 5/6821 |

OTHER PUBLICATIONS

International Search Report and Written Opinion from the International Searching Authority for corresponding International Application No. PCT/US2020/024915, dated Aug. 19, 2020; 19 pages.

Brinton et al., Electronic enhancement of tear secretion, Journal of Neural Engineering, Institute of Physics Publishing, Bristol, GB, vol. 13, No. 1, Published Dec. 11, 2015; 8 pages.

"Allergan TrueTear®." Allergan TrueTear®, www.truetear.com/, accessed Mar. 25, 2020.

Flowers, Brian. "Getting in the Ring." Glaucoma Today, accessed Mar. 25, 2020.

* cited by examiner

NON-INVASIVE PERIOCULAR DEVICE FOR DRY-EYE TREATMENT

CROSS-REFERENCE TO RELATED APPLICATION

This application claims the benefit of the filing date of, and priority to, U.S. Application No. 62/824,111, filed Mar. 26, 2019, the entire disclosure of which is hereby incorporated herein by reference.

BACKGROUND

A large number of people have Dry Eye Disease ("DED"), which includes symptoms of intense pain, stinging eyes, foreign body sensation, light sensitivity, blurriness, increased risk of infection, and possible vision loss.

DED is characterized by insufficient tear volume on the ocular surface of a patient, which is generally caused by insufficient tear production or excessive tear evaporation. Insufficient tear volume results in tear hyperosmolarity, which causes inflammation and nerve damage and can lead to progressive loss of tear production and quality.

Dry-eye symptoms vary based on a variety of factors. For example, dry-eye symptoms vary throughout a day in response to diurnal physiological variations in tear pH, intraocular pressure, corneal sensitivity, visual sensitivity, and melatonin production. For instance, corneal sensitivity is often significantly greater in the evening than compared to the morning. Longer term variations in dry-eye symptoms can be related to use of systemic medications, chronic disease (e.g., diabetes), hormonal changes, and aging. Changes to a patient's environment also contribute to dry-eye symptom variations. For example, dry-eye symptoms can increase due to low humidity of air-conditioned offices, winter heating, computer use, phone use, allergens, and contact lenses.

Current approaches to treatment of dry-eye symptoms do not or cannot account for the variety of factors that impact the severity and onset of the symptoms, as current treatment for DED is primarily eye-drop based and provides only limited episodic and temporary relief.

DETAILED DESCRIPTION

Figure 1:
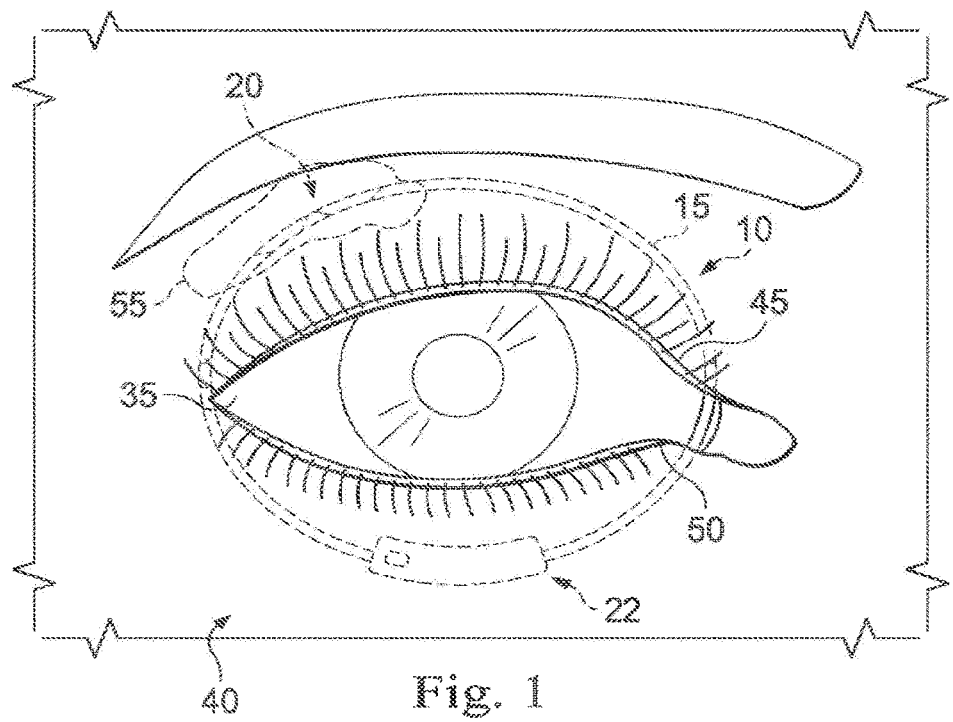
FIG. 1 is an illustration of a periocular device to be worn around an eye, and proximate to a lacrimal gland, of a user, according to an example embodiment.

The following disclosure provides many different embodiments or examples. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The present disclosure presents embodiments of a device with a unique form factor to provide dry-eye therapy. For example, embodiments of a ring-shaped periocular neurostimulator are presented for stimulating the lacrimal gland to stimulate tear production. In at least some embodiments, the periocular device rests on the surface of the eye, so no surgical procedures or implanted or implantable devices are needed for dry-eye therapy. Some advantages include that a patient can have specific, non-invasive personalized dry-eye therapy delivered seamlessly throughout the day, synchronized to the patient's natural circadian variation, and personalized to the patient's environment. Further, a form factor of the device allows for sensor placement at different points about the periphery or circumference of the device, allowing for closed-loop control of stimulation, based on measurements related to dryness of the eye, as discussed further herein.

A device generally referred to by the reference numeral 10, as illustrated in FIG. 1, is an example ring-shaped periocular device for neurostimulation. When mounted on the eye, the device 10 is not visible or noticeable to the user or others. Moreover, the device 10 does not obstruct the view of the user, as the device 10 does not extend over the pupil, iris, limbal ring, etc. As such, the device 10 can be used simultaneously with traditional vision correction devices, such as contact lenses and eye glasses. The device 10 is insertable in the periocular space and easily removable for cleaning and/or recharging. Thus, insertion and removal of the device 10 can be performed without the need for surgery. In some instances, the user can insert and remove the device 10 in his or her home. The device 10 also provides for hands-free stimulation. That is, as the device 10 includes electrodes for stimulating the lacrimal gland and a microcontroller that controls the stimulation, and the user is not required to perform any activity to activate the electrodes. The stimulation can be based on a predetermined schedule that is stored in the device 10 or can be in response to a detected or predicted dry eye condition. For example, while the user is performing another activity, such as viewing a graphical display of his or her mobile phone, the camera of the mobile phone may detect a blink rate that indicates the user is experiencing a dry-eye symptom. In response, the mobile phone wirelessly instructs the device 10 to activate the electrodes to stimulate the lacrimal gland. In some instances, the user is not aware of the detection, instruction, and activation. A user may utilize a device 10 in one eye or a device in each eye (i.e., a user may use two devices 10, one for each eye), as needed. For ease of description, the disclosure focuses on the application of device 10 to one eye, with the understanding that the disclosure may apply to both eyes of a user.

In an example embodiment and as illustrated in FIG. 1, the device 10 generally includes a wearable band or ring 15 and a gland stimulator assembly 20. In some embodiments, the stimulator assembly 20 is considered part of the ring 15, as the stimulator assembly 20 is attached physically and electrically to the ring. The term "ring" used herein refers generally to a substantially circular shape but it is not so limited and may refer to an elliptical shape circumscribing, and spaced from, portions of the eye, such as the limbal ring. Generally, the device 10 is configured to encircle the front of an eye 35 of a user 40 in the ocular fornix area. For example, the device 10 may be worn outside the periphery of a user's iris, circumscribing the iris, and spaced radially away from the iris. The device 10 is positioned such that the gland stimulator assembly 20 is in close enough proximity to a lacrimal gland 55 of the user 40 to stimulate tear production when electrical signals are applied to the stimulator assembly. As is understood in the art, electrical stimulation of a lacrimal gland 55 is known to increase tear production.

The disclosed devices, systems, and methods are for treating conditions of a patient's DED using a chronotherapeutic approach. The chronotherapeutic approach is implemented by the device 10, which delivers gland stimulation at the time when it is needed. That is, gland stimulation is synchronized with circadian rhythms, among other factors, in some embodiments. If the peak of symptoms occurs at daytime for example, gland stimulation can be performed just before or when the symptoms are worsening, depending on the delay between stimulation of the gland and production of additional tear fluid.

Figure 2:
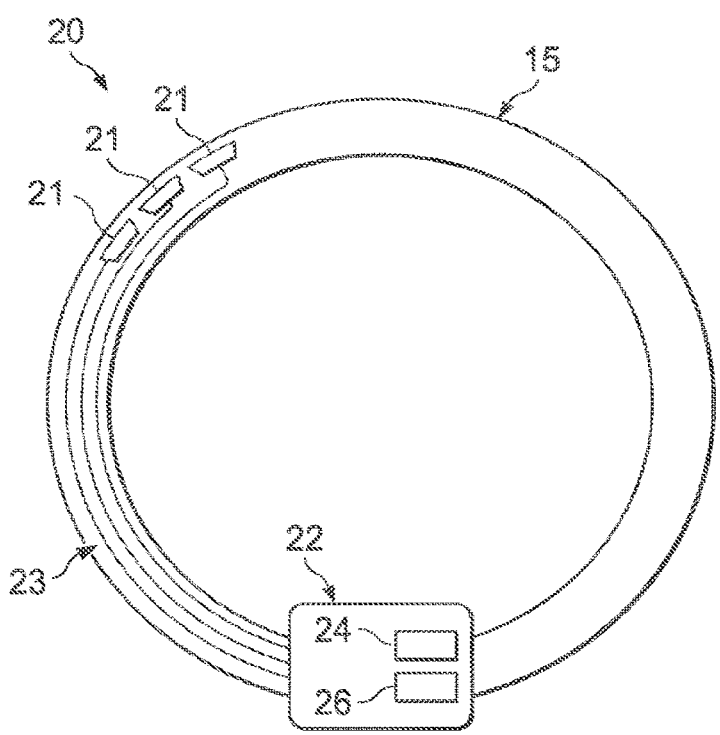
FIG. 2 is a diagrammatic illustration of the device of FIG. 1, according to an example embodiment.

As illustrated in FIG. 2, the gland stimulator assembly 20 generally includes electrodes 21, a microcontroller 22, and a lead assembly 23 that operably couples the electrodes 21 to the microcontroller 22. Generally, the microcontroller 22 also includes, or is operably coupled to, a power source 24 and a memory 26. In some embodiments and when the power source 24 includes a battery, such as a lithium thionyl chloride cell, the battery has terminals connected to the input of a voltage regulator that forms a portion of the microcontroller 22. The regulator smooths the battery output and supplies power to the microcontroller 22, which controls the programmable functions of the stimulator assembly 20, including known stimulation parameters such as pulse amplitude (measured as current or voltage, e.g., 500 µA to 25 mA), pulse frequency, pulse width, and on-time and off-time of the output pulses supplied to the electrodes 21. The microcontroller 22 is programmable in that a patient profile can be stored in the memory 26. Using the patient profile, the microcontroller 22 modulates the electrical activity of the lacrimal gland to produce the treatment regimen applicable to the patient. Timing signals for the logic and control functions of the generator are provided by the memory 26.

In some embodiments, the patient profile stored in the memory 26 includes a temporal model that details target stimulation parameters to be applied over a period of time. In some embodiments, the target stimulation parameters include a magnitude or charge density (e.g., current or voltage), frequency, pulse width, on-time, and off-time of the output pulses. The temporal model could detail a treatment program that is cycled daily, weekly, monthly, and/or seasonally. In some instances, the temporal model is based on a monitored eye condition of the patient/user, a charting of perceived symptoms by the patient/user, and/or a generic temporal model based on patient: age, sex, weight, geographical location, profession, activity level, or any combination thereof. Different combinations of stimulation parameters may be programmed into memory (e.g., by a clinician) and selectable by a patient. Patient selection of a combination of stimulation parameters may take place via a software application on a smartphone and communicated to the ring 15 via Bluetooth or other form of wireless communication. As other examples, the ring 15 may be configured for near-field communication or inductive telemetry for communication with a programming wand.

Figure 5:
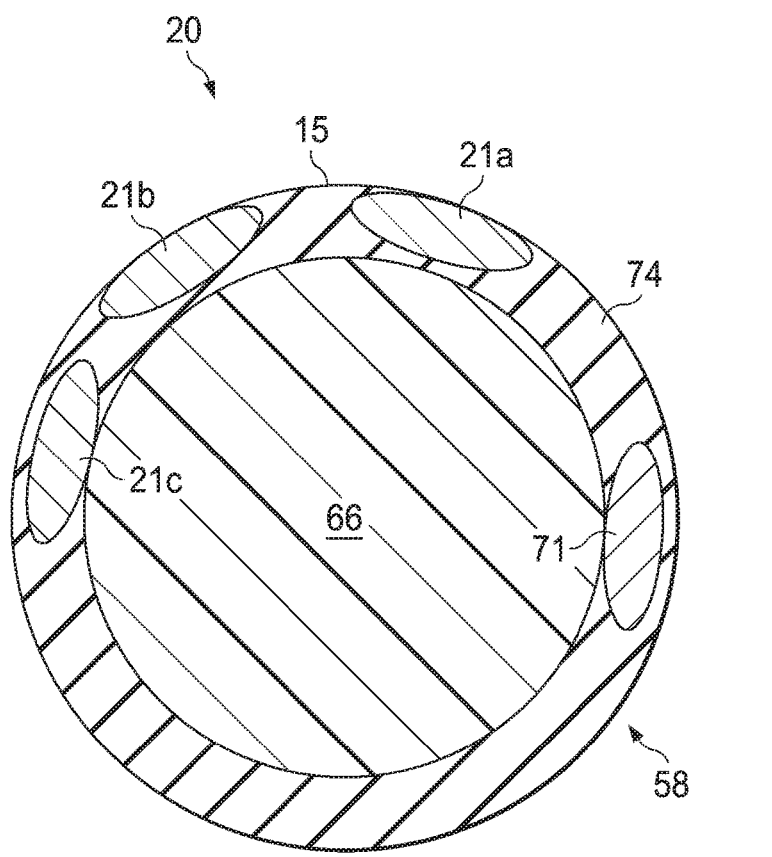
FIG. 5 is an illustration of a sectional view of the device of FIG. 1, according to an example embodiment.
Figure 6:
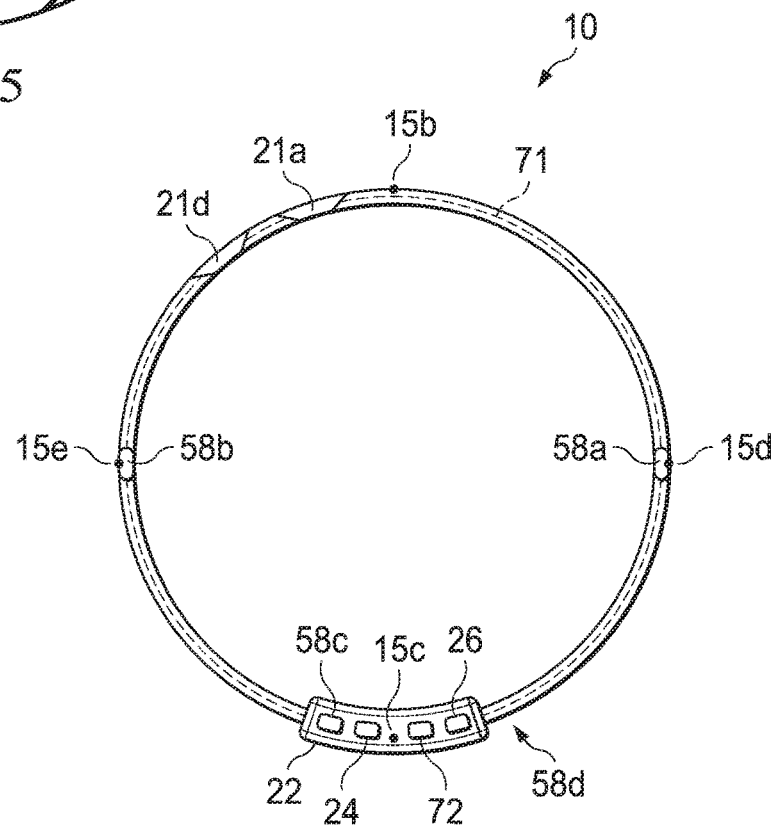
FIG. 6 is an illustration of a front view of the device of FIG. 1, according to an example embodiment.

In some embodiments, the electrodes 21 are located on the periphery of the ring 15 and are ideally located in apposition to the lacrimal gland 55 or nerve when the device 10 is worn by the user 40. That is, when the device 10 is worn by the user 40, the microcontroller 22 applies an output signal to the gland 55 via the lead assembly 23 and the electrodes 21. In some embodiments, the electrodes 21 are composed of a material including Pt, Pt/Ir alloys, Ir, and similar electrochemically stable, high-charge capacity metals and alloys. In some embodiments, direct stimulation of the lacrimal gland 55 via the gland stimulator assembly 20 dramatically increases tear production several fold. In some embodiments an as illustrated in FIGS. 5 and 6, the electrodes 21 are spaced along the ring 15. In some embodiments, the electrodes are spaced circumferentially along the ring 15, spaced radially along the ring 15, and/or spaced circumferentially along a cross-section of the ring 15. For example, and referring to FIG. 5, electrodes 21a and 21b are spaced circumferentially and aligned radially along a cross-section of the ring 15 while electrodes 21b and 21c are spaced circumferentially and radially along the cross-section of the ring 15. Referring to FIG. 6, electrodes 21a and 21d are spaced circumferentially along the ring 15. In some embodiments, the electrodes 21 may be configured as an electrode array for directing the generated electric field to more effectively stimulate the lacrimal gland.

In some instances, and as illustrated in FIGS. 3-6, the device 10 includes a sensor assembly 58 that detects a dry-eye symptom to form a closed-loop dry-eye treatment device. As such, the device 10 enables a customized stimulation profile for treatment of DED. The frequency and duration of dry-eye symptoms are specific to each person with DED because dry-eye symptoms are due to a wide variety of factors, such as, for example local environment, health-related issues, and time of day. As the device 10 detects and then treats the dry-eye symptoms, the device 10 is a closed-loop dry-eye treatment device 10. That is, the device 10 provides an automatic, customized treatment for DED and is a chronotherapeutic neural stimulation system. Electronic stimulation of the lacrimal gland 55 and nerve is performed in a controlled manner only when required and is based on physiological parameters measured by the device 10 and personalized or local environmental and health factors.

In some embodiments, the sensor assembly 58 includes one or more sensors and/or types of sensors. For example, the sensor assembly 58 includes sensors 58a, 58b, 58c, and 58d. For example, the sensor 58a and 58b form a tear film break-up ("TFBU") sensor system. Each of the sensors 58a and 58b is a small electrode that are located about 180 degrees apart on the periphery of the ring 15. The electrode material may be suitable metals including Pt, Pt/Ir alloys, Ir, and similar electrochemically stable metals. Generally, the sensors 58a and 58b measure resistivity of tear film that is located between the sensors 58a and 58b during application of a small alternating current signal (e.g., 1-100 mV Pk-Pk) at frequencies above 1 kHz. At frequencies above 1 kHz, the resultant signal is primarily a measure of the volumetric conductive path through tear fluid located on the eye 35 and as such is a function of the volume. As the tear film thins and breaks, a characteristic AC impedance can be measured and correlated to tear-film dynamics. These dynamics may include tear-film break-up time, rate of evaporation, and total available volume. A faster break-up time is an indicator of overall dryness, including potential effects of environmental factors. As such, the sensors 58a and 58b, when configured to measure TFBU time, determine stability of the tear film and determine evaporative dry eye based on resistivity of tear film within an area 70. The sensors 58a and 58b are not required to be positioned about 180 degrees apart on the periphery of the ring 15 and in some embodiments, the sensors 58a and 58b are spaced within 90 degrees (along the periphery of the ring 15) to measure TFBU time within an area smaller than the area 70. In some embodiments and when the sensors 58a and 58b are not spaced about 180 degrees apart, multiple pairings of sensors 58a and 58b are spaced around the periphery of the ring 15, with each pair of sensor measuring an area or a portion of the eye 35. Together, the multiple pairings of sensors are used to determine tear-film dynamics of the eye 35.

In some embodiments, the sensor 58c is or includes a microelectrode pH sensor that monitors tear pH levels, as tear osmolality and pH have been shown to correlate with dry eyes. In some embodiments, the sensor 58c is positioned along the ring 15 such that, when the ring 15 is positioned around the eye 35, the sensor 58c is positioned in the upper fornix, the lower fornix, and/or near the microcontroller 22 of the device 10 to ensure the sensor 58c remains in contact with the tear fluid. In some embodiments, the sensor 58c is factory-calibrated, but in other embodiments the microcontroller 22 makes patient-specific calibrations performed with standard tear sampling materials in a clinician's office or through at-home systems. In some embodiments, the upper fornix area is between the eye 35 and the eyelid 45, and the lower fornix area is between the eye 35 and the lower lid 50. However, in some instances the upper fornix area is any upper area (e.g., toward the eyebrow of the user) adjacent to the eye 35 and the lower fornix area is any lower area (e.g., toward the jaw of the user) adjacent to the eye 35.

In some embodiments and as illustrated in FIGS. 5 and 6, the sensor 58d is a blink sensor. That is, the sensor 58d is configured to monitor the blink rate of the user 40. Normal individuals display interblink times on average 4±2 seconds, while patients with dry eye display significantly decreased times averaging 1.5±0.9 seconds in an attempt to maximize the tear supply to the ocular surface. Thus, blink rate can be used to identify a dry eye condition. In particular, the decrease in interblink time for a specific patient can be measured throughout the day and used to correlate with diurnal variation in physiologic parameters such as corneal sensitivity. In some embodiments, the blink sensor 58d includes a resonant circuit. In particular, the circuit may be operated in a low-power configuration such that only start-up characteristics including start-up time or start-up current can be employed as means to detect blink induced changes in the resonant circuit response. In some embodiments, the resonant circuit includes an antenna 71 that is coupled to or forms a portion of the ring 15 and a capacitor 72 that is located within or near the electronics-containing body of the device, or the microcontroller 22. In some embodiments, the sensor 58d is an inductive-capacitive (LC) sensor that alters its capacitance in response to physical movement of the eyelid 45 (i.e., blinking), resulting in a shift in its resonant frequency. The change in resonant frequency is captured and processed by the integrated electronics thereby providing an input signal that is correlated with eyelid movements.

In some embodiments, the ring 15 forms an opening and has an inner diameter 15a (shown in FIG. 3) that is generally within the range of between about 24 mm to about 30 mm. However, the inner diameter 15a may be greater than 30 mm or less than about 24 mm. Generally, the ring 15 contacts an ocular surface of the eye, with a portion of the eye 35 extending through the opening of the ring 15. As illustrated, an innermost surface of the ring 15 is spaced from a limbal ring 60 of the eye 35 by a distance 73 (shown in FIG. 3) such that the ring 15 or device 10 does not extend over the iris and/or the limbal ring 60 of the eye 35. As such, both the iris and the limbal ring 60 are unobstructed by the device 10. Generally, the distance 73 varies with movement of the eye 35. That is, the ring 15 remains generally stationary even as the eye 35 and the ocular surface move. In some embodiments, placement and/or movement of the ring 15 is independent from the movement of the eye 35. In some embodiments, the ring 15 has a generally consistent cross-sectional shape and size. However, in other embodiments, a portion of the ring 15 has a cross-sectional shape that is different than a cross-sectional shape of another portion of the ring 15. Moreover, the inner diameter 15a of the ring 15 may vary independently from an outer diameter of the ring 15.

In some embodiments and as illustrated in FIG. 5, a portion of the gland stimulator assembly 20 and/or a portion of the sensor assembly 58 are disposed on a body of polymer substrate 66 to form the ring 15. The polymer substrate 66 may be composed of, or include, polymethylmethacrylate ("PMMA"), Parylene, Polyethylene terephthalate ("PET"), polyurethane, polyimide, rigid gas permeable fluorosilicone acrylate, liquid crystal polymer, silicon-based polymers, silicone acrylate and the like. Often, the polymer substrate 66, the gland stimulator assembly 20, and the sensor assembly 58 are encapsulated in a soft flexible biocompatible material 74 suitable for ocular wear, such as polymeric material like PMMA, polyhydroxyethylmethacrylate ("polyHEMA"), silicone hydrogel, silicon based polymers (e.g., flouro-silicon acrylate), silicone elastomer or combinations thereof. Generally, the device 10 is sufficiently flexible to be bent and placed under the eyelid 45 and the lower lid 50 of the user 40. Generally, the ring 15 forms a circular or ring shape with an uninterrupted circumference or periphery. However, in some embodiments, a gap is formed within the ring 15 to form a C shape. In some embodiments, the device 10 may have a visual marker on the device to assist a user when placing the device 10 on the eye so that electrodes are oriented adjacent to the lacrimal gland.

Generally, the gland stimulator assembly 20 and the sensor assembly 58 are operably coupled. Specifically, the sensor assembly 58 is operably coupled to the microcontroller 22 of the gland stimulator assembly 20. In an example embodiment, any one or more portions or sub-parts of the gland stimulator assembly 20 and the sensor assembly 58 are operably coupled. The device 10 may include any number of electrodes 21.

Figure 3:
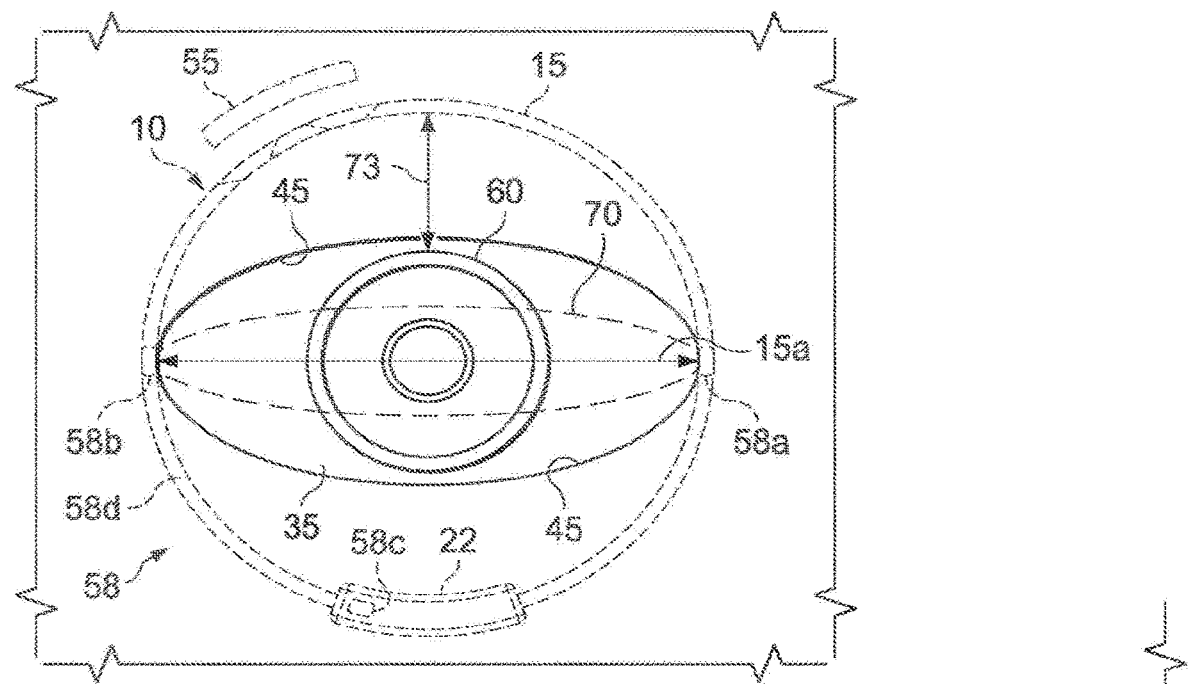
FIG. 3 is a front view of an illustration including the device, the eye, and the lacrimal gland of FIG. 1, according to an example embodiment.
Figure 4:
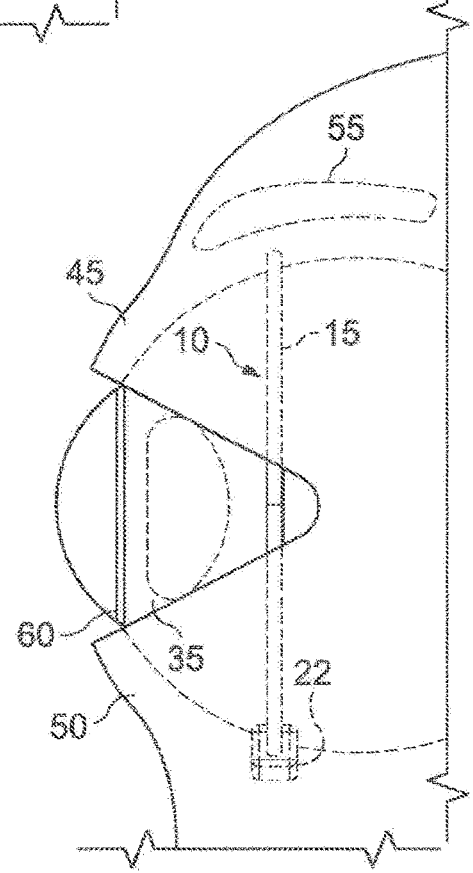
FIG. 4 is a side view of an illustration including the device, the eye, and the lacrimal gland of FIG. 1, according to an example embodiment.

As illustrated in FIGS. 3 and 4, the microcontroller 22 is positioned between the sensors 58a and 58b such that the microcontroller 22 is positioned between the lower lid 50 and the eye 35. In some embodiments, the cross-section of the ring 15 that is associated with the microcontroller 22 is thicker or otherwise larger than other cross-sections of the ring 15. In some embodiments, the portion of the ring 15 associated with the microcontroller 22 provides a friction-fit between the lower lid 50 and the eye 35 to anchor or position the ring 15 such that the electrodes 21 are proximate to or aligned with the gland 55.

In some embodiments, the power source 24 is a battery or the like. However, in some embodiments the power source 24 is the user or is generated by movement of the user. For example, in some embodiments, the power source is harvested energy from the body of the user 40 (e.g., harvested from motion, temperature, both motion and temperature).

In some embodiments and as illustrated in FIGS. 5 and 6, the antenna 71 is a looped antenna or a loop-shaped antenna that is formed within the ring 15 or otherwise coupled to the ring 15.

Referring to FIG. 6 (lead assembly 23 not shown), when viewed from the front view, the ring 15 is generally circular with a top point 15b associated with 0 degrees and an opposing bottom point 15c associated with 180 degrees. Two midpoints 15d and 15e, between the top and bottom points 15b and 15c, are associated with 90 degrees and 270 degrees respectively. In some embodiments, the sensor 58a is positioned at or near the midpoint 15d and the sensor 58b is positioned at or near the midpoint 15e. Moreover, the microcontroller 22 is positioned at or near the bottom point 15c with the electrodes 21 positioned between the midpoints 15e and 15b at a position associated between about 300 degrees and about 0 degrees when the device 10 is designed for placement in a right eye of the user 40. In some embodiments and when the device 10 is designed for placement in a left eye of the user 40, the electrodes 21 are positioned between the points 15b and 15d between about 0 degrees and about 60 degrees.

Figure 7:
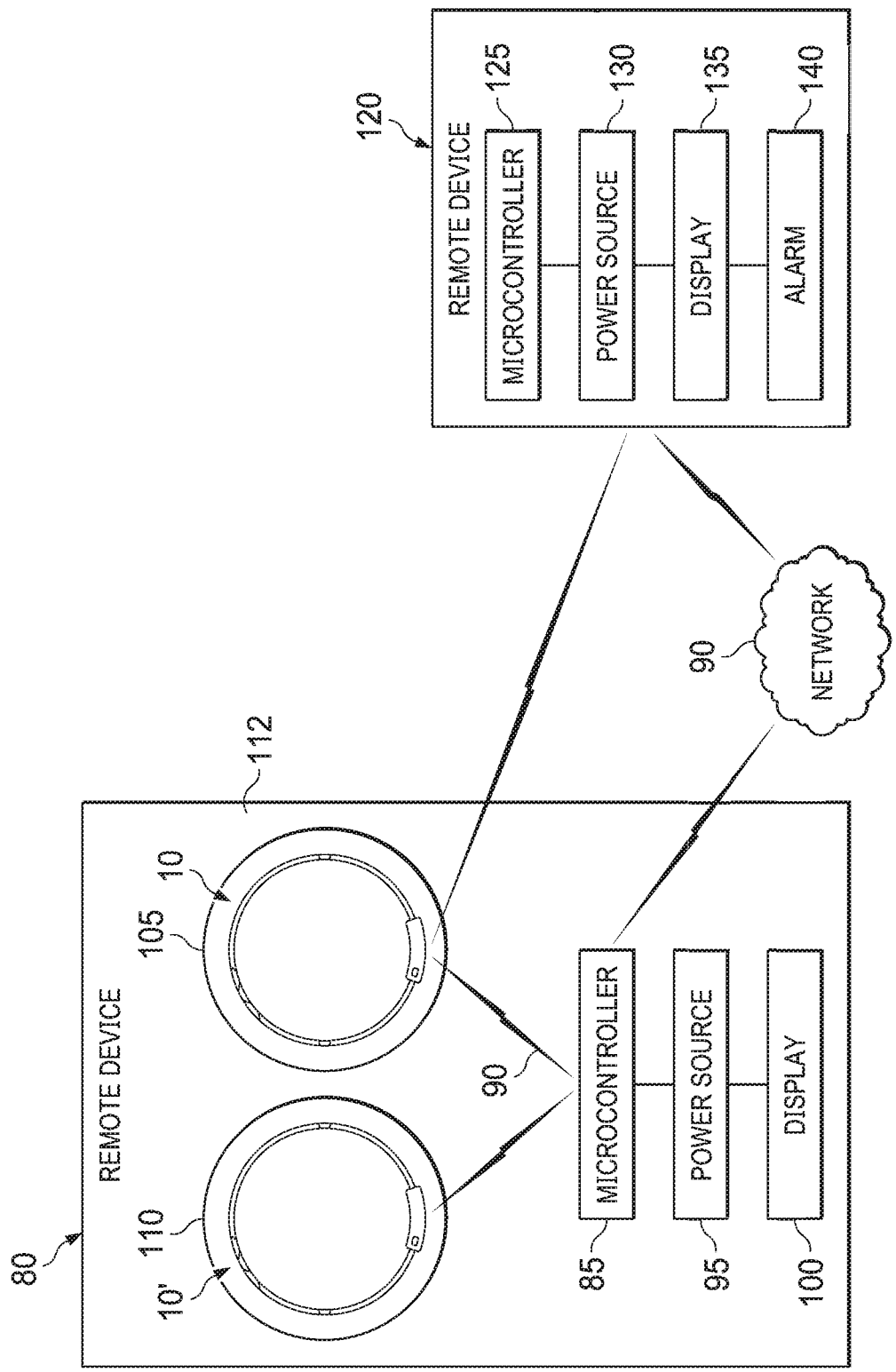
FIG. 7 is a diagrammatic illustration of the device of FIG. 1, a remote device, and another remote device connected via a network, according to an example embodiment.

As illustrated in FIG. 7, the device 10 is configured to be charged and/or cleaned by a remote device 80. Generally, the microcontroller 22 is configured for wireless communication with a microcontroller 85 of the remote device 80 via a network 90. In some embodiments, the remote device 80 includes the microcontroller 85, a power source 95, a display 100, and chambers 105 and 110 formed in a housing 112. Wireless connectivity may be provided by the microcontrollers 22 and 85, or a transceiver (not shown) coupled to each of the microcontrollers 22 and 85. In some embodiments, the remote device 80 is configured to temporarily house the device 10 and a similar device 10'. In some embodiments, the devices 10 and 10' are temporarily housed in the chambers 105 and 110, respectively, for cleaning of the sensor assembly 58 and/or the gland stimulator assembly 20, for recharging of the power source 24 such as recharging via the power source 95, and/or for transmitting data between the microcontroller 22 and the microcontroller 85. In some embodiments, the device 10 is associated with, or configured for, the right eye 35 of the user 40 and the device 10' is configured for the left eye of the user 40. In some embodiments, the microcontroller 22 is configured to communicate with another remote device 120 that includes a microcontroller 125, a power source 130, a display 135, and an alarm device 140. In some embodiments, the displays 135 and 100 are omitted. In some embodiments, the remote device 120 is a smart phone, tablet computer, personal digital assistant (PDA), or personal computing device (PCDs), or the like. In some embodiments, data exchanged between each of the devices 10 and 10' and the remote device 80 takes the form of any suitable technique, such as Bluetooth®, MICS, RF data, infrared, near field communication (NFC), etc. In some embodiments, the data exchanged includes or is related to the patient data, such as for example the temporal model, an updated temporal model, external factors, and any other useful information for operating a closed-loop therapy system.

Figure 8:
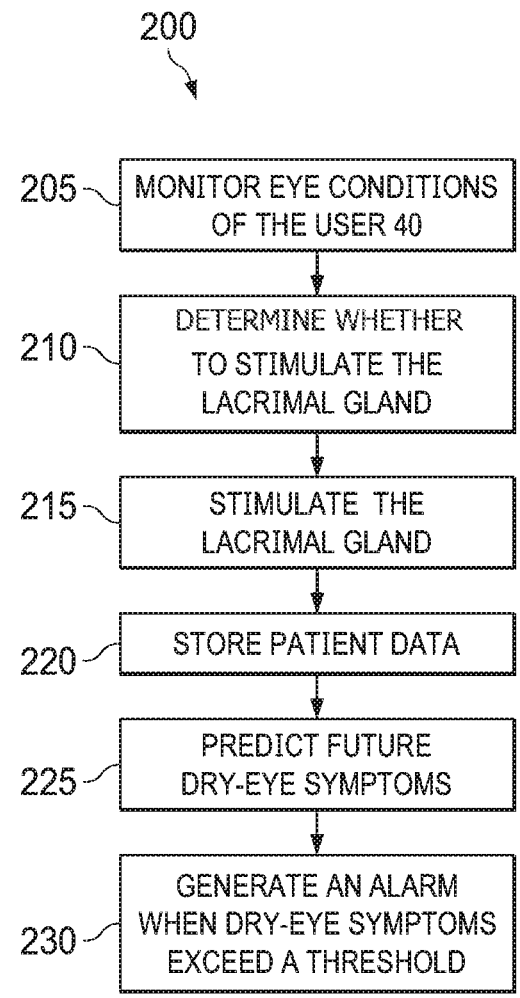
FIG. 8 is a flow chart illustrating a method of operating the device of FIGS. 1-7, according to an example embodiment.
Figure 9:
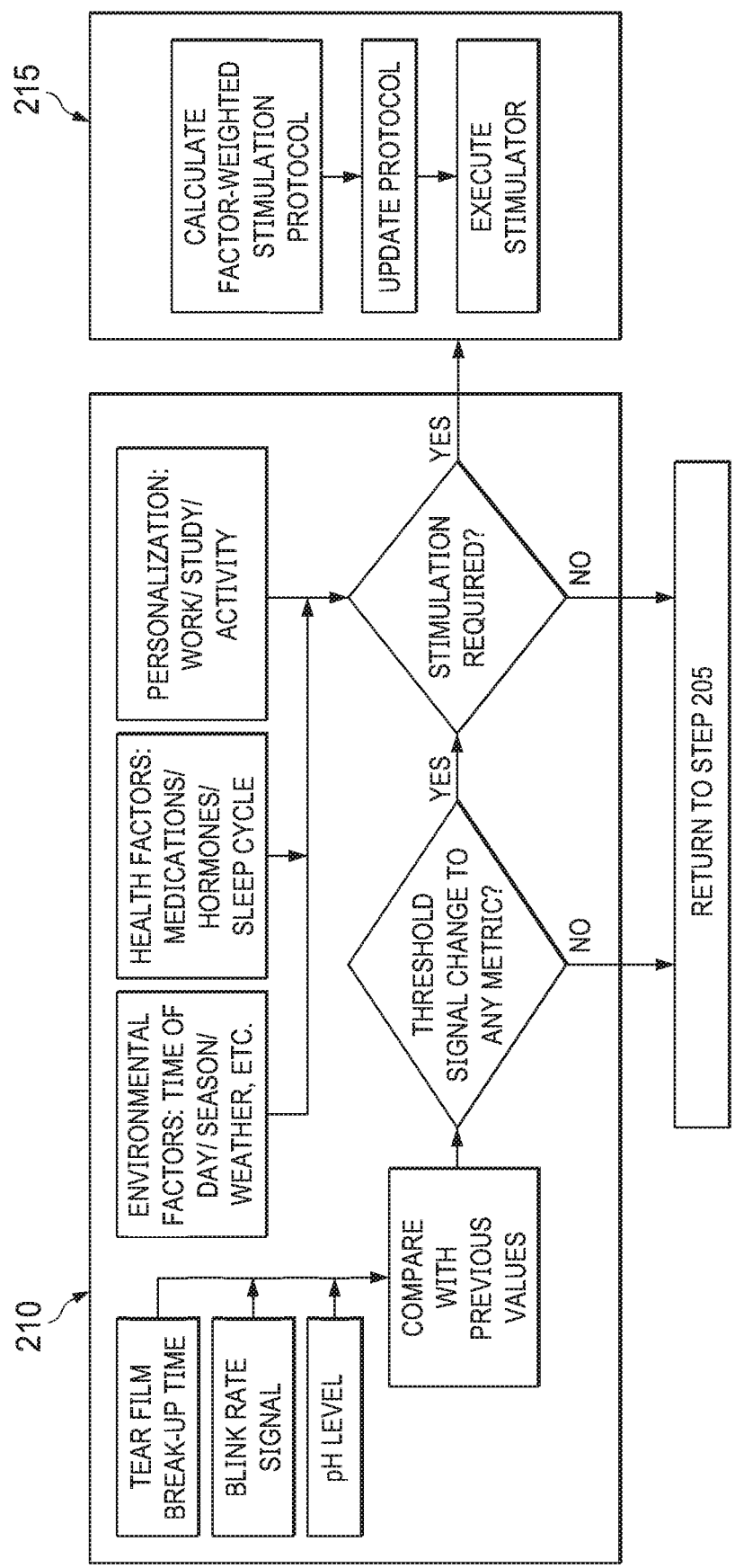
FIG. 9 is a flow chart illustrating a step in the method of FIG. 8, according to an example embodiment.

FIG. 8 is a flow chart illustrating a method 200 of operating the device 10 of FIGS. 1-7, according to an example embodiment. Generally, the method 200 includes monitoring eye conditions of the user 40 at step 205, determining whether to stimulate the lacrimal gland 55 at step 210, stimulating the lacrimal gland at step 215, storing patient data at step 220, predicting future dry-eye symptoms at step 225, and generating an alarm when dry-eye symptoms exceed a threshold at step 230.

At the step 205, and when the device 10 includes the sensor assembly 58, the device 10 detects the eye condition(s) of the patient or user 40 via the sensor assembly 58. Generally, the sensor assembly 58 continuously monitors eye condition(s) of the user 40 to generate user eye condition data. In some embodiments, the sensor assembly 58 is used to detect a dry eye condition based on the user eye condition data that includes: blink rate data generated by the sensor 58d; TFBU time data generated by the sensors 58a and 58b; and/or tear pH data generated by the sensor 58d. In some embodiments, the device 10 monitors all three parameters (i.e., blink rate, TFBU time, and tear pH), but in other embodiments, any variation or combination of the three parameters is continuously or periodically monitored. In some embodiments, the user eye condition data forms a portion of the patient data that is stored in the microcontroller 22. In other embodiments and when the sensor assembly 58 is omitted from the device, the eye condition(s) detected during the step 205 may be detected by the remote device 120 or another device.

Figure 10:
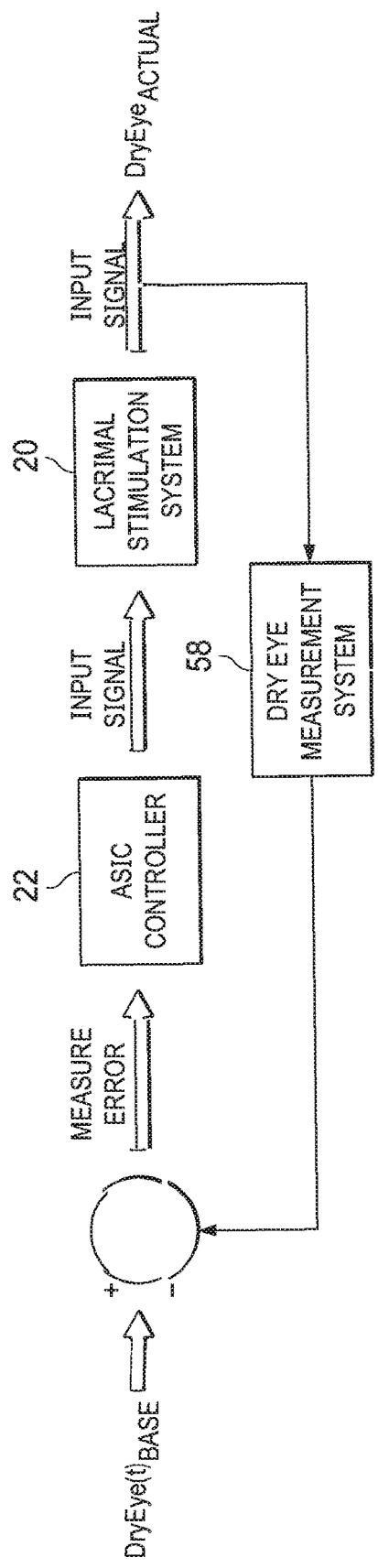
FIG. 10 is a diagrammatic illustration of a closed loop system formed by the device of FIG. 1 during the method of FIG. 9, according to an example embodiment.

At the step 210, the device 10 determines, using the user eye condition data (e.g., blink rate data, TFBU time data, and tear pH data), whether to stimulate the gland 55 using the gland stimulator assembly 20. As illustrated in FIG. 10, the step 210 can include the steps of receiving monitored eye condition values via the user eye condition data, comparing the values with previous values, determining whether there has been a threshold signal change to any metric, and then taking into account external factors such as local environmental factors, health factors, and personalization factors. Upon receiving the monitored eye condition values, the microcontroller 22 compares the most recently received values with historical or previously received values. In some embodiments, the microcontroller 22 determines a difference between the recently received values and the previous values. In some embodiments, the previous values are values received within a specific period of time (i.e., all previous values received in the last 2 hours), a specific number of most recently received values (i.e., the 1000 most recently received values), and/or the highest/lowest values received (i.e., highest blink rate associated with the user). In other embodiments, one of the previous values is a target value or baseline, and the difference is calculated against the target value. The difference may be an incremental difference based on the most recent value or may be a difference calculated based on maximum, minimum, average, or target of the previously received values. After the difference is identified, the microcontroller 22 determines if the difference exceeds a threshold. Generally, if the difference does not exceed the threshold, then stimulation is not required. If the difference exceeds the threshold, then the microcontroller 22 continues to determine if stimulation is required. In summary, the use of sensors, such as sensor assembly 58, on or in the device 10 provides for closed-loop stimulation that involves comparing measurements to desired values to determine whether and/or how to stimulate the lacrimal gland to yield tear production.

When determining if stimulation is required, the microcontroller 22 considers external factors that include environmental factors, health factors, and personalization factors of the user 40. The environmental factors include the time of day, the season, the weather, etc. The health factors include medications taken by the user 40, the hormones of the user 40 (administered or measured within the user 40), and the sleep cycle of the user 40. The personalization factors include whether the user 40 is assumed to be studying, working, or performing another activity. In some embodiments, the microcontroller 22 considers the external factors to determine whether exceeding the threshold is indicative of a true dry-eye symptom or is contributed to an external factor. For example, if the blink rate exceeds the threshold thereby indicating that a dry-eye symptom is present, but the user 40 is performing an activity that results in a higher blink rate, then the microcontroller 22 may determine that, in this instance, the blink rate exceeding the threshold does not correlate with a dry-eye symptom, but with the activity of the user 40. Thus, the microcontroller 22 performs a factor-weighted analysis using the external factors to determine whether the weighted difference exceeds the threshold and stimulation of the gland 55 is necessary or desired. However, in other embodiments and when the sensor assembly 58 is omitted from the device 10, the step 210 includes referencing the temporal model stored in the memory 26 and/or receiving instructions wirelessly.

At the step 215, the device 10 stimulates the gland 55 via the electrodes 21. Upon stimulation, tears are produced principally by the lacrimal gland 55 under the influence of the parasympathetic and sympathetic nerves. Electrical stimulation of the afferent and efferent nerves proximal to the lacrimal gland 55 can elicit a tear response. Efferent fibers synapse directly with the lacrimal gland acinar cells and trigger the release of water, electrolytes, and proteins from the lacrimal gland 55 onto the ocular surface. In some embodiments, the gland stimulator assembly 20 emits 10-100 Hz, 100-500 µs pulses, with charge density of 0.05-5.0 µC mm-2. Stimulation can be applied through biphasic charge-balanced waveforms. In some embodiments, the target stimulation parameters are modulated to achieve optimum response based on several factors including the patient's own physiology and environmental variables. In some embodiments and before stimulating the gland 55 via the electrodes 21, the microcontroller calculates the factor-weighted target stimulation parameters. That is, the microcontroller 22 considers the external factors and historical patient data to determine the strength and duration of stimulation that is required. In some embodiments, the historical patient data includes the patient's response to historical gland stimulation. That is, the microcontroller 22 monitored a change in the eye condition(s) using the sensor assembly 58 while simultaneously stimulating the lacrimal gland 55 using previous target stimulation parameters. The detected change in the eye condition(s) in response to stimulation using the previous target stimulation parameters forms a portion of the historical patient data. Thus, the device 10 is capable of refining or updating the previous target stimulation parameters to determine the target stimulation parameters, based on the patient's response to previous simulations. Moreover, the microcontroller 22 considers the external factors to determine the target stimulation parameters. That is, the microcontroller 22 not only performs a factor-weighted analysis using the external factors to determine whether the stimulation is required, but also performs a factor-weighted analysis using the external factors to determine the target stimulation parameters for the required stimulation. In some embodiments, the microcontroller 22 stores the target stimulation parameters and/or updates the temporal model using the target stimulation parameters before, during, or after stimulating the gland 55.

FIG. 10 illustrates a closed loop dry eye control system administered by the device 10 during the steps 205, 210, and 215. As illustrated, $DryEye(t)_{base}$ is the patient specific target tear hydration baseline. $DryEye_{actual}$ is the real-time dry-eye condition as measured by the sensor assembly 58. In this embodiment the microcontroller 22, which in some embodiments includes or is a proportional-integral-derivative ("PID") controller, first detects $DryEye_{actual}$ via the monitored data from the sensor assembly 58 and adjusts the amount of lacrimal stimulation administered by the electrodes 21 proportional to the magnitude and direction of the deviation error from $DryEye(t)_{base}$. The microcontroller 22 may compare against patient data recorded during the last 24 hours or month, for example. In some embodiments, the microcontroller 22 compares against patient data recorded during the last 24 hours, for example.

At step 220, the patient data, which includes the monitored data, the target stimulation parameters, the previous target stimulation parameters, and the external factors data (measured, assumed, or received by the user 40), is stored. As noted above, in some embodiments, the user/patient data is stored in the microcontroller 22. However, the user/patient data is also stored or received by the microcontroller 85 of the remote device 80 via the network 90 and/or stored or received by the microcontroller 125 of the remote device 120 via the network 90. As illustrated in FIG. 7, during standard device disinfection or charging times (e.g., weekly or monthly), the microcontroller 22 may upload and update the user/patient data, which may span months to years, to a cloud-based database via the microcontroller 85 and/or the microcontroller 125. This user/patient data can be used to update, customize, and generate predictive models to refine dry eye management over the course of hours to days. The models may include a variety of factors including historical, current, and expected or predicted external factors, which are used to generate predictive models. Thus, on-board prediction allows for optimized patient regimens, or temporal models, based on each patient's specific physiology. These metrics may include patient-specific parameters such as, for example, age, comorbidities, diabetes, hormonal changes (pregnancy, contraceptive use, and hormone replacement therapy), allergies, blink rate, tear generation rate, etc. In some embodiments, metrics also include monitoring medications and dosage (e.g., blood pressure medications (diuretics and beta-blockers), sleeping pills, antidepressants, anti-anxiety drugs, painkillers, antihistamines, and decongestants as well as some medications used to treat acne and Parkinson's disease). In some embodiments, metrics also include environmental factors such as, for example, dry indoor environments; air conditioning or heat; hospital environments; airplanes; other work environments; wind; smoke; fumes from chemicals; and sunlight. Patient metrics and patient data, when used with predictive models, are used to create and provide customized treatment for each patient that simultaneously addresses symptoms and compliance, which generally improves outcomes for DED patients.

In some embodiments, the remote device 120 requests confirmation that values classified as a dry-eye symptom coincided with a dry-eye symptom. The request for confirmation may be displayed on the display 135 of the remote device 120. The user 40 of the remote device 120 can provide confirmation via an input button located on the remote device 120. In some embodiments, a patient profile that includes the user/patient data and customized treatment plans for the user 40 is stored in one or more of the microcontrollers 22, 85, and/or 125 such that the patient profile is refined with every use of the device 10 by the user 40. In some instances, and when the device 10 is disposable or has a limited design life, the patient profile is stored in the microcontroller 85 or 125, and when a new device similar to the device 10 is paired with the remote device 80 or 120, the patient profile is capable of being uploaded or transferred to the new device.

At the step 225, a future dry-eye symptom is predicted using the microcontroller 22. Using historical user data and the patient profile, the microcontroller 22 identifies a trend of a value to predict an upcoming untreatable dry-eye symptom that may exceed the treatment capabilities of the device 10. In some embodiments, the device 10 monitors the duration and frequency of values that are classified as a dry-eye symptom and that are also treated or corrected via stimulation of the gland 55. The device 10 and/or the remote device 120 also determines if the duration of the detected dry-eye symptom is greater than a predetermined maximum duration. For example, dry-eye symptoms lasting longer than 2 hours (or another predetermined duration of time that is associated with potential damage to the eye 35) may be classified as a detected untreatable dry-eye symptom that requires intervention by the user 40.

At the step 230 and in some embodiments, the remote device 120 generates an alarm. Generally, the alarm is in response to the device 10 or the remote device 120 predicting and/or detecting an untreatable dry-eye symptom. In some embodiments, the remote device 120 generates different types of alarms, such as, for example the predicted or detected untreatable dry-eye symptom warning. Moreover, a first recommendation may be generated as well. For example, the first recommendation may be to administer eye drops to avoid potential damage to the eye 35, change ambient conditions, change activity, and the like. The recommendation includes an audible recommendation via a speaker (e.g., the alarm device 140) of the remote device 120 and/or a written message displayed on the display 135 of the remote device 120. In some embodiments, an alarm is generated by the device 10 without the remote device 120. For example, the device 10 may include a light-emitting diode which is activated to generate the alert, the device 10 may provide a vibration alert, or the device 10 may provide an electrical pulse that produces a physical sensation on the eye 35.

While in some embodiments the device 10 communicates with the remote device 80 and/or the remote device 120 when the device 10 is removed from periocular space, in other embodiments, the power source 24 is recharged while the device 10 is worn by the user 40. For example, the power source 24 could be charged by a power source that is positioned within a pair of glasses, hat, or ear piece that is capable of charging the power source 24 when worn by the user 40. In other embodiments, the device 10 communicates with the remote device 80 and/or the remote device 120 when the device 10 is worn by the user 40. In these cases, and when the remote device 120 is a phone or other mobile electronic device associated with the user 40, GPS data of the remote device 120, and thus the user 40, is communicated to the microcontroller 22. In some embodiments, the real-time location via the GPS data of the user 40 is considered by the microcontroller 22 as an external factor. In some embodiments, data received and monitored by the remote device 120 is communicated to the microcontroller 22 and is one of the external factors. In other embodiments, GPS data is considered by the microcontroller 125 when determining/updating the patient profile, which is then uploaded to the device 10. However, other types of location information, such as calendar event based means, cellular triangulation, WIFI source, user input, etc., can be considered by the microcontroller 125 and uploaded to the device.

In some embodiments, the electrodes 21 are spaced between the midpoints 15*d* and 15*e* such that the point 15*b* is positioned between electrodes 21. In some instances, the electrodes 21 are spaced around the entirety of the circumference of the ring 15. In some embodiments, the microcontroller 22 learns via selective stimulation of portions of the electrodes 21 whether the device 10 is positioned in the right or left eye and selectively activates the portion of the electrodes 21 that have been determined as proximate the lacrimal gland 55. Thus, one design of the device 10 is capable of being used in either eye of the user 40.

In some embodiments, the device 10 and/or the method 200 responds to the patient's current physiological state and provides optimum therapeutic stimulation of the lacrimal gland 55. In some embodiments, the device 10 and/or the method 200 does not block or affect vision in any way as the limbal ring 60 and an iris of the eye 35 extend through and beyond the opening of the ring 15. In some embodiments, the device 10 and/or the method 200 is compatible with all forms of vision correction (e.g., contact lenses, spectacles, etc.). In some embodiments, the device 10 and/or the method 200 generates data used for improved outcomes-based care models. In some embodiments, the device 10 and/or the method 200 targets stimulations both temporally and spatially to the lacrimal gland 55. In some embodiments, the device 10 and/or the method 200 can be used to achieve fully customizable stimulation paradigms from first-order constant stimulation profiles to on-demand pulsatile stimulation. Factors considered by the device 10 and/or the method 200 include circadian, seasonal, behavioral, and slowly varying variables that are currently not factored in any useful way into the management of dry eye. In some embodiments, the device 10 and/or the method 200 provides ambulatory hands-free and automatic operation that is invisible to the patient and others. In some embodiments, the device 10 and/or the method 200 monitors and treats dry eye discreetly without tethering or any additional body worn hardware. Generally, the device 10 allows for integrated dry-eye sensing, integrated, hands-free electronic lacrimal gland stimulation, and closed-loop operation based on patient-specific physiological parameters and personalized environmental and health factors.

In other embodiments, the microcontroller 125 is a battery operated hub with a processor. In other embodiments, the microcontroller 125 is omitted or replaced with a remote server (e.g., "the cloud"). Moreover, in some embodiments, the device 10 is at least capable of communicating with an application server. In some embodiments, a mobile application is stored in the memory of the microcontroller 125, and selectively displayed on the display 135, of the remote device 120 and/or in the memory, and selectively displayed on the display 100 of the remote device 80. The mobile application is in communication with the application server via the network 90. The user data and/or a summary thereof is received by the application server directly from the device 10 via the network 90. In some embodiments, the application server predicts/detects a potential dry-eye symptom that exceeds a maximum threshold amount and sends instructions to generate the alert to the remote device 120. In some embodiments, the alert includes a push notification displayed on the display 135 of the remote device 120. Thus, while the collection of the user data is performed at the device 10, there are multiple locations at which the predicting/detecting can occur, such as, for example, in the microcontroller 125 of the remote device 120, in the microcontroller 22, or in a remote server.

In some embodiments, the measurements and combinations of measurements that are classified as an indication of dry-eye symptom are refined based upon an aggregation of data from multiple users, with the data having been received at the remote server. That is, in some embodiments, data from multiple users can be used to refine the factor-weighted analysis performed by the microcontrollers 22, 85, and/or 125.

In some embodiments, the device 10, the remote device 80, and/or the remote device 120 are configured to operate in a sleep or idle mode.

In some embodiments and as noted above, the sensor assembly 58 is omitted from the device 10 and the microcontroller 22 activates the electrodes 21 based on a predetermined schedule that is stored in the device 10, regardless of the eye conditions. In some embodiments, the sensor assembly 58 is omitted from the device 10 and the microcontroller 22 activates the electrodes 21 in response to a wireless transmission or command from the remote device 120. That is, the remote device 120 may be monitoring conditions and wirelessly instructing the microcontroller 22 to activate the electrodes 21. As such and in some embodiments, the remote device 120 includes a sensor assembly, such as a camera, which measures the eye conditions of the user. For example, and when the user is looking at the remote device 120, the remote device 120 detects a blink rate that indicates a dry-eye condition and the remote device 120 instructs the microcontroller 22 to activate the electrodes 21.

In an example embodiment, the network 90 includes the Internet, one or more local area networks, a Bluetooth low energy network, one or more wide area networks, one or more cellular networks, one or more wireless networks, one or more voice networks, one or more data networks, one or more communication systems, and/or any combination thereof.

Generally, any creation, storage, processing, and/or exchange of user data associated the method, apparatus, and/or system disclosed herein is configured to comply with a variety of privacy settings and security protocols and prevailing data regulations, consistent with treating confidentiality and integrity of user data as an important matter. For example, the apparatus and/or the system may include a module that implements information security controls to comply with a number of standards and/or other agreements. In some embodiments, the module receives a privacy setting selection from the user and implements controls to comply with the selected privacy setting. In other embodiments, the module identifies data that is considered sensitive, encrypts data according to any appropriate and well-known method in the art, replaces sensitive data with codes to pseudonymize the data, and otherwise ensures compliance with selected privacy settings and data security requirements and regulations.

In some embodiments, the device 10 automatically, dynamically, and predictively adjusts therapeutic levels of DED treatment throughout the day/week/month based on real-time measurement of the patient's dry-eye physiology leveraged against personalized environmental and health factors. With electronics integration into the periocular-mounted device 10, patient specific therapies are tailored through direct measurement of physiological indicators such as blink rate, tear film break-up time and tear pH that are monitored by the sensor assembly 58. In some embodiments, the sensor assembly 58 includes—in addition to as a substitute for the sensors 58*a*, 58*b*, 58*c*, and 58*d*-one or more thermal sensors that monitors the eye surface temperature, one or more sensors that monitors the meibum content (i.e., the oils that prevent rapid tear evaporation), and/or one or more sensors that monitor corneal and conjunctival inflammation biomarkers.

Figure 11:
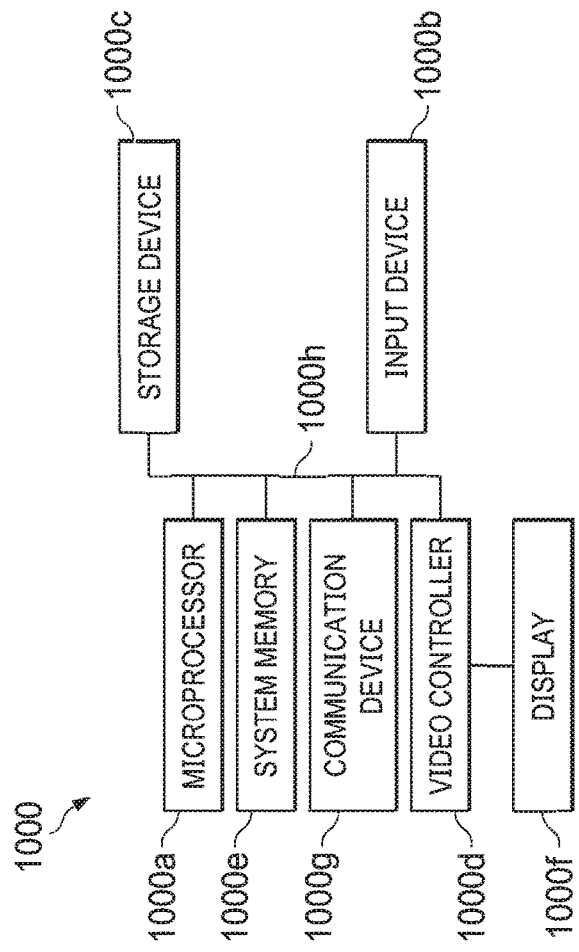
FIG. 11 is a diagrammatic illustration of a node for implementing one or more example embodiments of the present disclosure, according to an example embodiment.

In an example embodiment, as illustrated in FIG. 11 with continuing reference to FIGS. 1-10, an illustrative node 1000 for implementing one or more of the example embodiments described above and/or illustrated in FIGS. 1-10 is depicted. The node 1000 includes a microprocessor 1000*a*, an input device 1000*b*, a storage device 1000*c*, a video controller 1000*d*, a system memory 1000*e*, a display 1000*f*, and a communication device 1000*g* all interconnected by one or more buses 1000*h*. In several example embodiments, the storage device 1000*c* may include a hard drive, CD-ROM, optical drive, any other form of storage device and/or any combination thereof. In several example embodiments, the storage device 1000*c* may include, and/or be capable of receiving, a CD-ROM, DVD-ROM, or any other form of computer-readable medium that may contain executable instructions. In several example embodiments, the communication device 1000*g* may include a modem, network card, or any other device to enable the node to communicate with other nodes. In several example embodiments, any node represents a plurality of interconnected (whether by intranet or Internet) computer systems, including without limitation, personal computers, mainframes, PDAs, smartphones, and cell phones.

In several example embodiments, one or more of the components of the systems described above and/or illustrated in FIGS. 1-10, include at least the node 1000 and/or components thereof, and/or one or more nodes that are substantially similar to the node 1000 and/or components thereof.

In several example embodiments, one or more of the applications, systems, and application programs described above and/or illustrated in FIGS. 1-10, include a computer program that includes a plurality of instructions, data, and/or any combination thereof; an application written in, for example, Arena, Hypertext Markup Language (HTML), Cascading Style Sheets (CSS), JavaScript, Extensible Markup Language (XML), asynchronous JavaScript and XML (Ajax), and/or any combination thereof; a web-based application written in, for example, Java or Adobe Flex, which in several example embodiments pulls real-time information from one or more servers, automatically refreshing with latest information at a predetermined time increment; or any combination thereof.

In several example embodiments, a computer system typically includes at least hardware capable of executing machine readable instructions, as well as the software for executing acts (typically machine-readable instructions) that produce a desired result. In several example embodiments, a computer system may include hybrids of hardware and software, as well as computer subsystems.

In several example embodiments, hardware generally includes at least processor-capable platforms, such as client-machines (also known as personal computers or servers), and hand-held processing devices (such as smartphones, tablet computers, personal digital assistants (PDAs), or personal computing devices (PCDs), for example). In several example embodiments, hardware may include any physical device that is capable of storing machine-readable instructions, such as memory or other data storage devices. In several example embodiments, other forms of hardware include hardware subsystems, including transfer devices such as modems, modem cards, ports, and port cards, for example.

In several example embodiments, software includes any machine code stored in any memory medium, such as RAM or ROM, and machine code stored on other devices (such as flash memory, or a CD ROM, for example). In several example embodiments, software may include source or object code. In several example embodiments, software encompasses any set of instructions capable of being executed on a node such as, for example, on a client machine or server.

In several example embodiments, combinations of software and hardware could also be used for providing enhanced functionality and performance for certain embodiments of the present disclosure. In an example embodiment, software functions may be directly manufactured into a silicon chip. Accordingly, it should be understood that combinations of hardware and software are also included within the definition of a computer system and are thus envisioned by the present disclosure as possible equivalent structures and equivalent methods.

In several example embodiments, computer readable mediums include, for example, passive data storage, such as a random-access memory (RAM) as well as semi-permanent data storage such as a compact disk read only memory (CD-ROM). One or more example embodiments of the present disclosure may be embodied in the RAM of a computer to transform a standard computer into a new specific computing machine. In several example embodiments, data structures are defined organizations of data that may enable an embodiment of the present disclosure. In an example embodiment, a data structure may provide an organization of data, or an organization of executable code.

In several example embodiments, any networks and/or one or more portions thereof may be designed to work on any specific architecture. In an example embodiment, one or more portions of any networks may be executed on a single computer, local area networks, client-server networks, wide area networks, internets, hand-held and other portable and wireless devices, and networks.

In several example embodiments, a database may be any standard or proprietary database software. In several example embodiments, the database may have fields, records, data, and other database elements that may be associated through database specific software. In several example embodiments, data may be mapped. In several example embodiments, mapping is the process of associating one data entry with another data entry. In an example embodiment, the data contained in the location of a character file can be mapped to a field in a second table. In several example embodiments, the physical location of the database is not limiting, and the database may be distributed. In an example embodiment, the database may exist remotely from the server and run on a separate platform. In an example embodiment, the database may be accessible across the Internet. In several example embodiments, more than one database may be implemented.

In several example embodiments, a plurality of instructions stored on a non-transitory computer readable medium may be executed by one or more processors to cause the one or more processors to carry out or implement in whole or in part the above-described operation of each of the above-described example embodiments of the system, the method, and/or any combination thereof. In several example embodiments, such a processor may include one or more of the microprocessor 1000a, any processor(s) that are part of the components of the system, and/or any combination thereof, and such a computer readable medium may be distributed among one or more components of the system. In several example embodiments, such a processor may execute the plurality of instructions in connection with a virtual computer system. In several example embodiments, such a plurality of instructions may communicate directly with the one or more processors, and/or may interact with one or more operating systems, middleware, firmware, other applications, and/or any combination thereof, to cause the one or more processors to execute the instructions.

A periocular ring configured to be worn on an eye of a user is disclosed that includes a plurality of electrodes spaced along the periocular ring; a microcontroller; and a lead assembly extending along at least a portion of the periocular ring; wherein the lead assembly extends between the microcontroller and the plurality of electrodes to operably couple the plurality of electrodes to the microcontroller; and wherein the microcontroller is configured to activate the plurality of electrodes via the lead assembly to stimulate a lacrimal gland of the user. In one embodiment, the plurality of electrodes is spaced circumferentially along the periocular ring. In one embodiment, the plurality of electrodes is spaced radially along the periocular ring. In one embodiment, the plurality of electrodes is spaced circumferentially along a cross-section of the periocular ring. In one embodiment, the periocular ring has an opening that defines an innermost diameter; and wherein, when the periocular ring is worn on the eye of the user, a portion of the eye extends through the opening of the periocular ring. In one embodiment, the innermost diameter is greater than a diameter of a limbal ring of the eye. In one embodiment, the microcontroller is configured to activate the electrodes based on a temporal model that comprises a target magnitude, a target frequency, and a target pulse width of output pulse(s) applied to the plurality of electrodes; and the temporal model is based on a user profile associated with the user. In one embodiment, the ring includes a power source operably coupled to the microcontroller and the plurality of electrodes to supply the output pulse(s) applied to the plurality of electrodes.

A periocular assembly configured to be worn on an eye of a user and circumscribe an iris of the user is disclosed and includes a plurality of electrodes spaced along the periocular assembly; a first microcontroller comprising a memory, wherein a temporal model associated with the user is stored in the memory; and a lead assembly extending along at least a portion of the periocular assembly; wherein the lead assembly extends between the first microcontroller and the plurality of electrodes to operably couple the plurality of electrodes to the first microcontroller; wherein the periocular assembly is positioned in the upper and lower fornix of the eye of the user such that the plurality of electrodes is proximate a lacrimal gland of the user. In one embodiment, the first microcontroller is configured to activate the plurality of electrodes to stimulate the lacrimal gland of the user based on the temporal model associated with the user; the periocular assembly further comprises a second microcontroller that is spaced from the periocular assembly; and the second microcontroller is configured to: update the temporal model associated with the user based on external factors associated with the user; wherein the external factors associated with the user comprises: data associated with health factors associated with the user; data associated with environmental factors associated with a local environment of the user, and/or activity data associated with activities performed by the user; and transmit the temporal model to the first microcontroller. In one embodiment, the periocular assembly has an opening that defines an innermost diameter; and when the periocular assembly is worn on the eye of the user, a portion of the eye extends through the opening of the periocular assembly. In one embodiment, the innermost diameter is greater than a diameter of a limbal ring of the eye. In one embodiment, the plurality of electrodes is spaced circumferentially along the periocular assembly. In one embodiment, the plurality of electrodes is spaced radially along the periocular assembly. In one embodiment, the plurality of electrodes is spaced circumferentially along a cross-section of the periocular assembly.

A method of stimulating a lacrimal gland of a user using a periocular device is disclosed and includes positioning the periocular device between an eyelid and an eye of the user; wherein the periocular device comprises: a ring configured to be worn on the eye of the user; and a stimulator assembly comprising: a plurality of electrodes spaced along the ring; a microcontroller comprising a memory, wherein stimulation parameters are stored in the memory; and a lead assembly extending along at least a portion of the ring; wherein the lead assembly extends between the microcontroller and the plurality of electrodes to operably couple the plurality of electrodes to the microcontroller; wherein the periocular device is positioned in the eye of the user such that the plurality of electrodes is proximate the lacrimal gland of the user; and activating, using the microcontroller and based on the stimulation parameters, the plurality of electrodes to stimulate the lacrimal gland of the user. In one embodiment, the plurality of electrodes is spaced circumferentially along the ring. In one embodiment, the plurality of electrodes is spaced radially along the ring. In one embodiment, the plurality of electrodes is spaced circumferentially along a cross-section of the ring. In one embodiment, the ring has an opening that defines an innermost diameter; and wherein, when the ring is worn on the eye of the user, a portion of the eye extends through the opening of the ring. In one embodiment, the innermost diameter is greater than a diameter of a limbal ring of the eye. In one embodiment, the stimulation parameters comprise a target magnitude, a target frequency, and a target pulse width of output pulse(s) applied to the electrodes; and activating, using the microcontroller and based on the stimulation parameters, the plurality of electrodes comprises activating the plurality of electrodes via output pulse(s) at the target magnitude, at target frequency, and at target pulse width. In one embodiment, the stimulation parameters are based on a user profile associated with the user. In one embodiment, the stimulation parameters comprise a predetermined stimulation schedule; and wherein activating, using the microcontroller, and based on the stimulation parameters, the plurality of electrodes to stimulate the lacrimal gland of the user is in accordance with the predetermined stimulation schedule.

It is understood that variations may be made in the foregoing without departing from the scope of the present disclosure.

In several example embodiments, the elements and teachings of the various illustrative example embodiments may be combined in whole or in part in some or all of the illustrative example embodiments. In addition, one or more of the elements and teachings of the various illustrative example embodiments may be omitted, at least in part, and/or combined, at least in part, with one or more of the other elements and teachings of the various illustrative embodiments.

Any spatial references such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above.

In several example embodiments, while different steps, processes, and procedures are described as appearing as distinct acts, one or more of the steps, one or more of the processes, and/or one or more of the procedures may also be performed in different orders, simultaneously and/or sequentially. In several example embodiments, the steps, processes and/or procedures may be merged into one or more steps, processes and/or procedures.

In several example embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

Although several example embodiments have been described in detail above, the embodiments described are example only and are not limiting, and those skilled in the art will readily appreciate that many other modifications, changes and/or substitutions are possible in the example embodiments without materially departing from the novel teachings and advantages of the present disclosure. Accordingly, all such modifications, changes and/or substitutions are intended to be included within the scope of this disclosure as defined in the following claims. In the claims, any means-plus-function clauses are intended to cover the structures described herein as performing the recited function and not only structural equivalents, but also equivalent structures. Moreover, it is the express intention of the applicant not to invoke 35 U.S.C. § 112, paragraph 6 for any limitations of any of the claims herein, except for those in which the claim expressly uses the word "means" together with an associated function.

I claim:

1. A periocular ring configured to be worn on an eye of a user comprising:

the periocular ring having an opening;
  wherein, when the periocular ring is worn on the eye of the user, a portion of the eye extends through the opening of the periocular ring;
a plurality of stimulating electrodes spaced along the periocular ring, wherein the plurality of stimulating electrodes includes a pair of stimulating electrodes configured to stimulate a lacrimal gland of the user;
a plurality of sensors spaced along the periocular ring; and
a microcontroller operably coupled to the plurality of stimulating electrodes and the plurality of sensors;
  wherein the microcontroller is configured to activate the plurality of stimulating electrodes to stimulate a lacrimal gland of the user;
  wherein at least one of the plurality of stimulating electrodes is located at a first radial location of the periocular ring and extends over a first portion of a cross-sectional circumference of the periocular ring at the first radial location, and wherein at least one of the plurality of sensors is located at a second radial location of the periocular ring and extends over a second portion of the cross-sectional circumference of the periocular ring at the second radial location, wherein the second portion of the cross-sectional circumference of the periocular ring is different from the first portion of the cross-sectional circumference of the periocular ring.

2. The periocular ring of claim 1, further comprising a lead assembly extending between the microcontroller and the plurality of stimulating electrodes to operably couple the plurality of stimulating electrodes to the microcontroller.

3. The periocular ring of claim 1, wherein the opening defines an innermost diameter that is greater than a diameter of a limbal ring.

4. The periocular ring of claim 1,
wherein the microcontroller is configured to activate the plurality of stimulating electrodes based on a temporal model that comprises a target magnitude, a target frequency, and a target pulse width of output pulse(s) applied to the plurality of stimulating electrodes; and
wherein the temporal model is based on a user profile associated with the user.

5. The periocular ring of claim 1, wherein the plurality of stimulating electrodes is spaced circumferentially along the periocular ring.

6. The periocular ring of claim 1, wherein the periocular ring has a plurality of points comprising:
a top point;
a bottom point opposite the top point; and
a first midpoint between the top point and the bottom point;
wherein at least one electrode of the pair of stimulating electrodes is positioned between the top point and the first midpoint; and
wherein the microcontroller is positioned at the bottom point.

7. A periocular assembly configured to be worn on an eye of a user and circumscribe an iris of the user, the periocular assembly comprising:
a periocular ring;
a plurality of stimulating electrodes spaced along the periocular assembly, wherein the plurality of stimulating electrodes includes a pair of stimulating electrodes configured to stimulate a lacrimal gland of the user;
a plurality of sensors spaced along the periocular assembly;
a first microcontroller comprising a memory;
wherein a temporal model associated with the user is stored in the memory; and
a lead assembly extending along at least a portion of the periocular assembly;
wherein the lead assembly extends between the first microcontroller and the plurality of stimulating electrodes to operably couple the plurality of stimulating electrodes to the first microcontroller;
wherein the periocular assembly is configured to be positioned in the eye of the user so that the at least one electrode of the pair of stimulating electrodes is positioned proximate to the lacrimal gland and the first microcontroller is positioned between a lower lid of the user and the eye; and
wherein the first microcontroller is configured to activate the plurality of stimulating electrodes to stimulate the lacrimal gland of the user based on the temporal model associated with the user;
wherein at least one of the plurality of stimulating electrodes is located at a first radial location of the periocular assembly and extends over a first portion of a cross-sectional circumference of the periocular assembly at the first radial location, and
wherein at least one of the plurality of sensors is located at a second radial location of the periocular assembly and extends over a second portion of the cross-sectional circumference of the periocular assembly at the second radial location, wherein the second portion of the cross-sectional circumference of the periocular assembly is different from the first portion of the cross-sectional circumference of the periocular assembly.

8. The periocular assembly of claim 7,
wherein the first microcontroller of the periocular assembly is configured to communicate with a second microcontroller that is spaced from the periocular assembly; and
wherein the second microcontroller is configured to:
update the temporal model associated with the user based on external factors associated with the user;
wherein the external factors associated with the user comprises:
data associated with health factors associated with the user;
data associated with environmental factors associated with a local environment of the user, and/or
activity data associated with activities performed by the user; and
transmit the temporal model to the first microcontroller.

9. The periocular assembly of claim 7,
wherein the periocular assembly has an opening that defines an innermost diameter; and
wherein, when the periocular assembly is worn on the eye of the user, a portion of the eye extends through the opening of the periocular assembly.

10. The periocular assembly of claim 9, wherein the innermost diameter is greater than a diameter of a limbal ring of the eye.

11. A method of stimulating a lacrimal gland of a user using a periocular device that is positioned between an eyelid and an eye of the user;
wherein the periocular device comprises:
a ring configured to be worn on the eye of the user;
a plurality of sensors spaced along the periocular device; and
a stimulator assembly comprising:
a plurality of stimulating electrodes spaced along the ring, wherein the plurality of stimulating electrodes includes a pair of stimulating electrodes configured to stimulate the lacrimal gland; and
a microcontroller operably coupled to the plurality of stimulating electrodes and comprising a memory;
wherein stimulation parameters are stored in the memory;
wherein the periocular device is positioned in an upper and lower fornix of the eye of the user so that the at least one electrode of the pair of stimulating electrodes is positioned proximate to the lacrimal gland; and
wherein at least one of the plurality of stimulating electrodes is located at a first radial location of the periocular device and extends over a first portion of a cross-sectional circumference of the periocular device at the first radial location, and
wherein at least one of the plurality of sensors is located at a second radial location of the periocular device and extends over a second portion of the cross-sectional circumference of the periocular device at the second radial location, wherein the second portion of the cross-sectional circumference of the periocular device is different from the first portion of the cross-sectional circumference of the periocular device; and wherein the method comprises activating, using the microcontroller and based on the stimulation parameters, the plurality of stimulating electrodes to stimulate the lacrimal gland of the user.

12. The method of claim 11, wherein the plurality of stimulating electrodes is spaced circumferentially along the ring.

13. The method of claim 11, wherein the ring has an opening that defines an innermost diameter; and wherein, when the ring is worn on the eye of the user, a portion of the eye extends through the opening of the ring.

14. The method of claim 13, wherein the innermost diameter is greater than a diameter of a limbal ring of the eye.

15. The method of claim 11, wherein the stimulation parameters comprise a target magnitude, a target frequency, and a target pulse width of output pulse(s) applied to the plurality of stimulating electrodes; and wherein activating, using the microcontroller and based on the stimulation parameters, the plurality of stimulating electrodes comprises activating the plurality of stimulating electrodes via output pulse(s) at the target magnitude, at target frequency, and at target pulse width.

16. The method of claim 11, wherein the stimulation parameters are based on a user profile associated with the user.

17. The method of claim 11, wherein the stimulation parameters comprise a predetermined stimulation schedule; and wherein activating, using the microcontroller and based on the stimulation parameters, the plurality of stimulating electrodes to stimulate the lacrimal gland of the user is in accordance with the predetermined stimulation schedule.

* * * * *